United States Patent [19]

Alker et al.

[11] Patent Number: 5,192,765
[45] Date of Patent: Mar. 9, 1993

[54] CERTAIN AMINES WHICH ARE MUSCARINIC RECEPTOR ANTAGONISTS

[75] Inventors: David Alker; Robert J. Bass, both of Birchington; Peter E. Cross, Canterbury, all of England

[73] Assignee: Pfizer Inc., New York, N.Y.

[21] Appl. No.: 687,913

[22] PCT Filed: Oct. 16, 1989

[86] PCT No.: PCT/EP89/01230

§ 371 Date: Jun. 6, 1991

§ 102(e) Date: Jun. 6, 1991

[87] PCT Pub. No.: WO90/04583

PCT Pub. Date: May 3, 1990

[30] Foreign Application Priority Data

Oct. 17, 1988 [GB] United Kingdom ............ 8824262.3

[51] Int. Cl.$^5$ ................ C07C 217/10; C07C 217/12; A16K 31/135
[52] U.S. Cl. .................................... 514/255; 514/357; 514/437; 514/438; 514/431; 514/450; 514/452; 514/455; 514/466; 514/469; 514/648; 514/651; 544/336; 544/408; 546/334; 549/12; 549/27; 549/72; 549/75; 549/350; 549/354; 549/362; 549/396; 549/437; 549/443; 549/462; 564/317; 564/352

[58] Field of Search ............... 564/317, 352; 549/350, 549/354, 362, 396, 437, 443, 462, 12, 72, 75, 27; 514/648, 651, 450, 431, 452, 437, 466, 469, 438, 255, 357, 455; 544/336, 408; 546/334

[56] References Cited

U.S. PATENT DOCUMENTS 2,455,949 12/1948 Rieveschl, Jr. .................... 564/317
4,097,528 6/1978 Porta et al. ........................ 564/317
4,246,201 1/1981 Borzatta ............................ 564/317

FOREIGN PATENT DOCUMENTS 650652 8/1965 Belgium .
A02646 12/1970 Switzerland .
1219609 1/1971 United Kingdom .

*Primary Examiner*—Bernard Dentz
*Attorney, Agent, or Firm*—Peter C. Richardson; Paul H. Ginsburg; Grover F. Fuller, Jr.

[57] ABSTRACT

Amines of the following formula:

$$R^1-O-CH_2-\underset{\underset{R^3}{|}}{\overset{\overset{R^2}{|}}{C}}-\underset{}{\overset{\overset{R^4}{|}}{N}}-(CH_2)_m-Y-R$$

where the variables are defined in the specification are useful in the treatment of diseases associated with altered motility and/or tone of smooth muscle.

13 Claims, No Drawings

CERTAIN AMINES WHICH ARE MUSCARINIC RECEPTOR ANTAGONISTS

This invention relates to certain amine derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

According to the invention there are provided compounds of the formula:

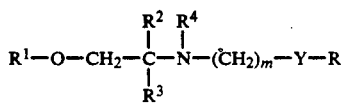
(I)

and their pharmaceutically acceptable salts, wherein $R^1$ is a group of the formula:

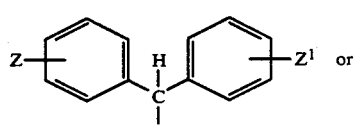

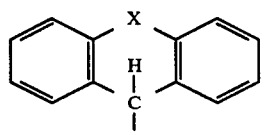

wherein
Z and $Z^1$ are each independently hydrogen, halo or $C_1$-$C_4$ alkyl;
X is —$(CH_2)_2$—, —CH=CH—, —$CH_2$—S—, —$CH_2$—O—, —S— or —O—; Y is a direct link, O or S;
$R^2$ and $R^3$ are each independently $C_1$-$C_4$ alkyl or together represent —$(CH_2)_p$— where p is 2, 3, 4 or 5;
$R^4$ is H or $C_1$-$C_4$ alkyl;
m is 1, 2 or 3, with the proviso that when m is 1, Y is a direct link; and
R is a group of the formula:

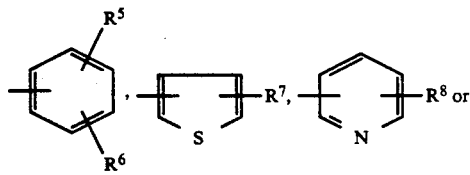

where

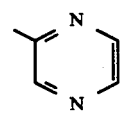

either $R^5$ and $R^6$ are each independently hydrogen, $C_1$-$C_4$ alkyl, hydroxy-($C_1$-$C_4$ alkyl), hydroxy, $C_1$-$C_4$ alkoxy, halo, halomethyl, nitro, cyano, sulphamoyl, —CO($C_1$-$C_4$ alkyl), —OCO($C_1$-$C_4$ alkyl), —$CO_2$($C_1$-$C_4$ alkyl), carboxy, —$(CH_2)_q$$CONR^9R^{10}$, —$(CH_2)_q$$OCONR^9R^{10}$, —$(CH_2)_q$$NR^{11}R^{12}$ or —$NHSO_2NH_2$ in which $R^9$ and $R^{10}$ are each independently H or $C_1$-$C_4$ alkyl, q is 0, 1 or 2, and either $R^{11}$ and $R^{12}$ are each independently H or $C_1$-$C_4$ alkyl or $R^{11}$ is hydrogen and $R^{12}$ is —$SO_2$($C_1$-$C_4$ alkyl), —CO($C_1$-$C_4$ alkyl) or —CONH($C_1$-$C_4$ alkyl); or
$R^5$ and $R^6$, when attached to adjacent carbon atoms, together represent a group of the formula —O$(CH_2)_r$O— where r is 1, 2 or 3, —O$(CH_2)_2$— or —$(CH_2)_3$—; $R^7$ is H, $C_1$-$C_4$ alkyl or —$CONH_2$; and
$R^8$ is H, $C_1$-$C_4$ alkyl or $C_1$-$C_4$ alkoxy.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy. The preferred halomethyl groups are trifluoromethyl and bromomethyl.

Preferred groups for $R^1$ include:

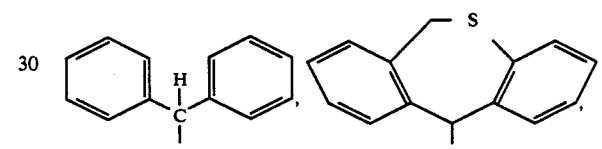

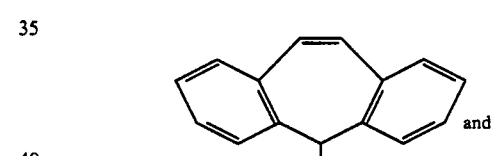

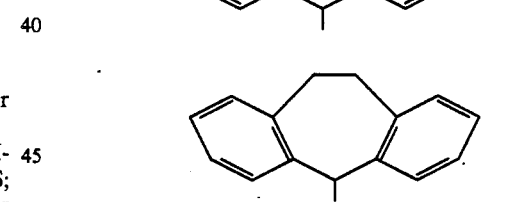

Y is preferably a direct link or O.
m is preferably 2. p is preferably 4 or 5, most preferably 4.
$R^2$ and $R^3$ are preferably each methyl or are taken together and represent —$(CH_2)_4$— or —$(CH_2)_5$—.
$R^4$ is preferably H or $CH_3$. Z and $Z^1$ are preferably H.
When R is said optionally substituted phenyl group, then it preferably has the formula:

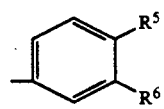

where $R^5$ and $R^6$ are as defined for formula (I).
When R is said optionally substituted thiophene group, it is preferably unsubstituted 2- or 3-thienyl.
$R^8$ is preferably hydrogen.
More preferably, R is a group of the formula:

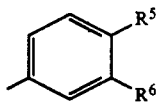

where either one of $R^5$ and $R^6$ is hydrogen and the other is hydrogen, $C_1$-$C_4$ alkoxy, $C_1$-$C_4$ alkyl, hydroxy, hydroxymethyl, halo, sulphamoyl, —CO($C_1$-$C_4$ alkoxy), carboxy, carbamoyl, —NHSO$_2$($C_1$-$C_4$ alkyl), —CH$_2$NHSO$_2$($C_1$-$C_4$ alkyl), —CO($C_1$-$C_4$ alkyl), halomethyl, cyano, nitro, or aminomethyl; or $R^5$ and $R^6$ together represent —OCH$_2$O—, —O(CH$_2$)$_2$O—, —O(CH$_2$)$_2$— or —(CH$_2$)$_3$—.

Most preferably, R is

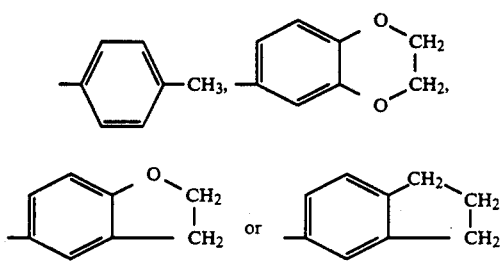

The preferred compounds have the formula:

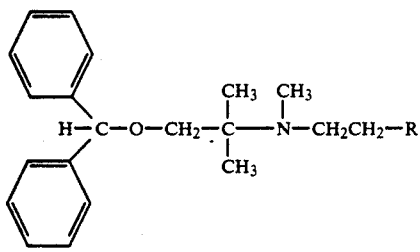

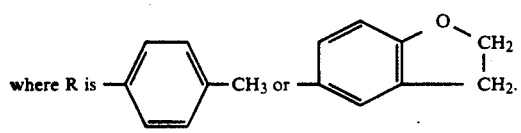

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ether, and recovering the acid addition salt either as a precipitate, or by evaporation of the solution.

The compounds of the formula (I) can be prepared by a number of routes, including the following:

Route A

This can be illustrated as follows:

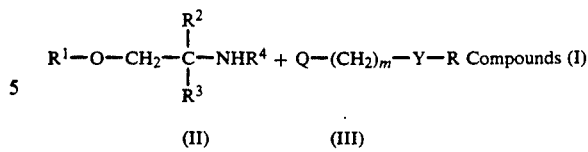

R, $R^1$, $R^2$, $R^3$, $R^4$, Y and m are as defined for formula (I) and Q is a leaving group, e.g. Br, Cl, I, $C_1$-$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, triethylamine or pyridine, and in a suitable organic solvent, e.g. acetonitrile, at up to the reflux temperature. Reaction temperatures of 60°-120° C. are generally desirable and it is most convenient to carry out the reaction under reflux. Iodo is generally the most suitable leaving group but since the starting materials (III) are generally most conveniently available as chlorides or bromides, the reaction is often most suitably carried out using the compound (III) as a chloride or bromide but in the presence of an iodide such as sodium or potassium iodide. In the preferred technique, the compounds (II) and (III), (III) being in bromide or chloride form, are refluxed together in acetonitrile in the presence of sodium or potassium carbonate and sodium or potassium iodide. The product (I) can be isolated and purified conventionally.

The starting materials of the formula (II) can be obtained by conventional procedures such as those described in Preparations 1 to 5. The starting materials of the formula (III) are in general known compounds which are either commercially available or can be prepared by conventional techniques. The preparation of the novel starting materials of the formula (III) used in the Examples is described in the Preparations 9 to 11.

Route B

This route can be illustrated as follows:

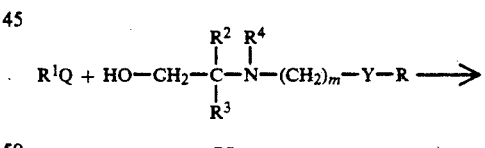

Compounds (I)

R, $R^1$, $R^2$, $R^3$, $R^4$, Y and m are as defined for formula (I) and Q is a leaving group such as described in Route A. In this route, Q is preferably Cl or Br. The presence of an acid acceptor such as sodium or potassium carbonate, triethylamine or pyridine is preferable. Where the compound (V) is fairly reactive, then the reaction will proceed to completion at room temperature. If necessary (generally when $R^1$ is an optionally substituted benzhydryl group), the reaction mixture can be heated at up to, say, 160° C., to accelerate the rate of reaction. The reaction can be carried in a suitable organic solvent, e.g. methylene chloride. The compound (I) can be isolated and purified conventionally.

The starting materials (V) can be prepared conventionally, e.g. by the techniques described in Preparations 6 to 8. The starting materials of the formula (IV) are either known compounds or can be prepared conventionally, e.g. by halogenation of the corresponding known hydroxy compounds.

Route C

This route is useful for preparing compounds in which R is 2- or 4- pyridyl or pyrazinyl, Y is a direct link, and m is 2, and can be illustrated as follows:

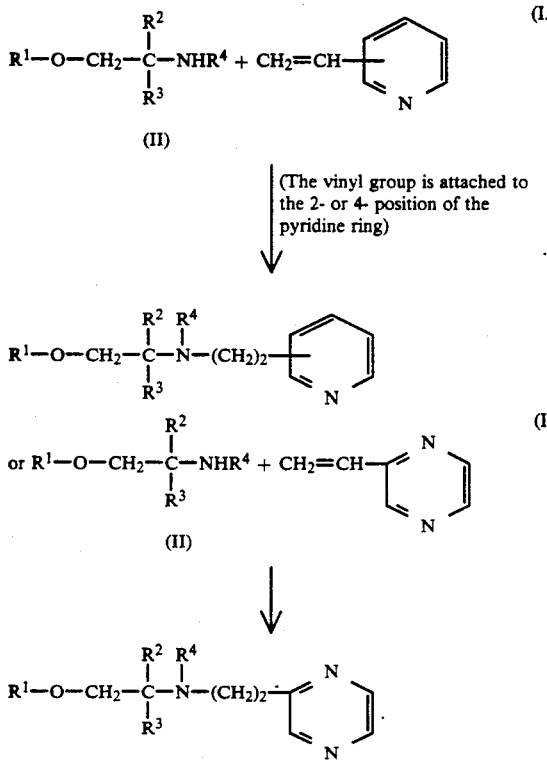

In the above, $R^1$, $R^2$, $R^3$ and $R^4$ are as defined for formula (I).

The reaction is typically carried out with heating at up to 160° C., preferably 80° to 140° C., in a suitable organic solvent, e.g. 1-butanol. The use of a basic (preferably a strong base which is soluble in an organic solvent such as N-benzyltrimethylammonium hydroxide ["Triton B"]) or acidic (preferably a $C_1$-$C_4$ alkanoic acid) catalyst is necessary. The preferred procedure is to reflux the reactants in the organic solvent in the presence of a basic catalyst such as "Triton B".

Route D

Compounds of the formula (I) in which $R^4$ is methyl can also be prepared by reaction of compounds of the formula (I) in which $R^4$ is H with aqueous HCHO/NaCNBH$_3$ in, e.g., methanol at room temperature.

Some of the compounds of the formula (I) in which R is a substituted phenyl group can be converted to other compounds of the formula (I) as follows:

(a) A —$CO_2$($C_1$-$C_4$ alkyl) substituent on the phenyl group can be reduced to —$CH_2OH$. Lithium aluminium hydride is the most suitable reducing agent. The reaction is typically carried in a suitable organic solvent, e.g. ether, at between 0° and room temperature. It is generally most convenient to use the starting material in the form of its methyl or ethyl ester.

(b) A hydroxy substituent on the phenyl group can be converted to —OCO($C_1$-$C_4$ alkyl) by acylation using a $C_1$-$C_4$ alkanoyl chloride or bromide or a $C_1$-$C_4$ alkanoic anhydride. The presence of an acid acceptor is preferable. The reaction is typically carried out at about room temperature in a suitable organic solvent, e.g. dioxan.

(c) A —CO($C_1$-$C_3$ alkyl) substituent on the phenyl group can be reduced to a substituent of the formula —CH(OH) ($C_1$-$C_3$ alkyl). Suitable reducing agents include sodium borohydride and lithium aluminium hydride. The reaction is typically carried out at between 0° and room temperature in a suitable organic solvent, e.g. methanol in the case of sodium borohydride and ether or tetrahydrofuran in the case of lithium aluminium hydride. Sodium borohydride is the preferred reducing agent.

(d) A carboxy substituent can be converted to —CONR$^9$R$^{10}$ by reaction with oxalyl or thionyl chloride to form the acid chloride followed by reaction with ammonia or the appropriate amine R$^9$R$^{10}$NH.

(e) A carbamoyl substituent can be reduced to aminomethyl, e.g. using lithium aluminium hydride, typically in tetrahydrofuran.

(f) A —$CO_2$($C_1$-$C_4$ alkyl) substituent, preferably —$CO_2CH_3$, can be converted to —CONR$^9$R$^{10}$ by reaction with ammonia or the appropriate amine R$^9$R$^{10}$NH. When R$^9$ and R$^{10}$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60° to 100° C., is generally necessary. For volatile amines, the reaction is best carried out in a bomb.

(g) A nitro substituent on the phenyl group can be reduced to amino by conventional means. The preferred reducing agent is stannous chloride dihydrate and the reaction is typically carried out in an organic solvent such as ethanol under reflux.

(h) A substituent of the formula —$(CH_2)_qNH_2$ can be converted to —$(CH_2)_qNHSO_2$($C_1$-$C_4$ alkyl) by reaction with a $C_1$-$C_4$ alkanesulphonyl chloride or bromide or $C_1$-$C_4$ alkanesulphonic anhydride. The presence of an acid acceptor such as pyridine, triethylamine, sodium bicarbonate or sodium or potassium carbonate, is preferable. It is often most convenient, particularly when a sulphonyl chloride is used, to carry out the reaction in pyridine, the pyridine functioning as both the solvent and the acid acceptor. Heating is not usually necessary: normally the reaction will proceed at a satisfactory rate at room temperature.

(i) A chloro- or bromo-methyl substituent can be converted to aminomethyl by reaction with ammonia, e.g. in methanol at about room temperature.

(j) A substituent of the formula —$(CH_2)_qNH_2$ where q is 0, 1 or 2 can be converted to —$(CH_2)_qNHCO$($C_1$-$C_4$ alkyl) by reaction with a $C_1$-$C_4$ alkanoyl chloride or bromide or alkanoic anhydride of the formula ($C_1$-$C_4$ alkyl.CO)$_2$O. The reaction can be carried out similarly to (b) above.

(k) An amino substituent on the phenyl group can also be converted to sulphamoylamino by reaction with sulphamide, typically under reflux in an organic solvent such as dioxan.

(l) A hydroxy substituent can be converted to $C_1$-$C_4$ alkoxy firstly by reaction with a strong base such as sodium hydride, and then by reaction with a $C_1$-$C_4$ alkyl iodide. The reaction is preferably carried out at about room temperature in a solvent such as dimethylformamide.

(m) A hydroxy or hydroxyalkyl substituent of the formula —$(CH_2)_qOH$ where q is 0, 1 or 2 can be converted to —$(CH_2)_qOCONH(C_1$-$C_4$ alkyl) by reaction with a $C_1$-$C_4$ alkyl isocyanate. The reaction is typically carried out at about room temperature in a solvent such as methylene chloride.

(n) A hydroxymethyl substituent on the phenyl group can be converted to —$CH_2NR^{11}R^{12}$ where $R^{11}$ and $R^{12}$ are each H or $C_1$-$C_4$ alkyl by reaction firstly with thionyl chloride ad secondly with ammonia or the appropriate amine $R^{11}R^{12}NH$. The reaction with thionyl chloride is typically carried out with heating, preferably under reflux, in a solvent such as methylene chloride. The reaction with ammonia or the amine is typically carried out at about room temperature in a solvent such as ethanol.

(o) An acetyl substituent can be converted to —C(OH)($CH_3$)$_2$ by reaction with methyllithium, methylmagnesium bromide, methylmagnesium iodide or methylmagnesium chloride. The reaction is typically carried out in a solvent such as ether at a temperature of from 0° C. to room temperature.

(p) An iodo substituent can be converted to $C_1$-$C_4$ alkoxycarbonyl by reaction, typically at about room temperature, with carbon monoxide in a $C_1$-$C_4$ alkanol containing a base [e.g. potassium carbonate] and a palladium (II) catalyst [e.g. bis(triphenylphosphine)palladium (II) chloride].

(q) A cyano substituent on the phenyl group can be reduced to aminomethyl, typically by catalytic hydrogenation, e.g. using $H_2$/Pd/C in ethanol containing a small amount of concentrated hydrochloric acid.

(r) A substituent of the formula —$(CH_2)_qNH_2$ where q is 0, 1 or 2 can be converted to a substituent of the formula —$(CH_2)_qNHCONH(C_1$-$C_4$ alkyl) by reaction with a $C_1$-$C_4$ alkyl isocyanate. The reaction is typically carried out at about room temperature in a solvent such as methylene chloride.

(s) A $C_1$-$C_4$ alkoxy substituent, preferably methoxy, can be converted to hydroxy by treatment with a $C_1$-$C_4$ alkanethiol in the presence of a strong base, e.g. sodium hydride. The reaction is typically carried out by refluxing the reactants in a suitable solvent, e.g. dimethylformamide. Butanethiol is the preferred thiol. and (t) A —$CO_2(C_1$-$C_4$ alkyl) substituent can be hydrolysed to carboxy by conventional techniques, such as by heating with sodium hydroxide in dioxan/water.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined ($pA_2$ value — Arunlakshana and Schild (1959), Brit. J. Pharmacol., 14, 48-58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heat rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered along, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes any novel intermediates as used herein, especially those of the formulae (II) and (V).

The invention yet further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The following Examples, in which all temperatures are in °C., illustrate the invention:

EXAMPLE 1

2-[2-(Benzodioxan-6-yl)ethylamino]-1-(diphenylmethoxy)-2-methylpropane

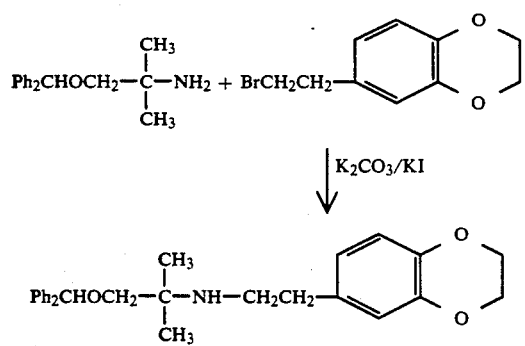

A mixture of 2-amino-1-diphenylmethoxy-2-methylpropane (369 mg — see Preparation 1), 6-(2-bromoethyl)benzodioxan (243 mg — see Preparation 10), potassium carbonate (415 mg) and potassium iodide (166 mg) in acetonitrile (40 ml) was heated under reflux for 48 hours and evaporated. The residue was partitioned between ethyl acetate and water and the organic layer was washed with water, dried over sodium sulphate and evaporated. The residue was purified by chromatography on silica (7 g) using ethyl acetate plus 0–5% methanol as the eluant. Appropriate fractions were combined and evaporated to give the title compound as a colourless oil which was characterised as a hemihydrate (130 mg, 31%).

Analysis %: Found: C,76.2; H,7.4; N,3.1; $C_{27}H_{31}NO_3.0.5H_2O$ requires: C,76.0; H7.6; N,3.3.

EXAMPLE 2

1-Diphenylmethoxy-2-(4-methoxyphenethylamino)-2-methylpropane

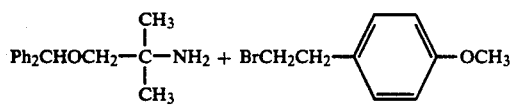

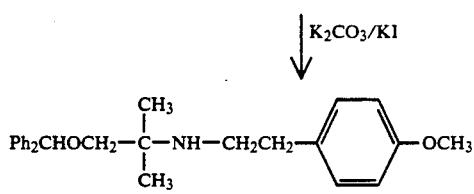

The title compound was prepared as described in Example 1 using 4-methoxyphenethyl bromide and 2-amino-1-diphenylmethoxy-2-methylpropane (see Preparation 1). The title compound was obtained as a colourless oil (378 mg, 33%).

Analysis %: Found: C,78.7; N,8.0; N,4.1; $C_{26}H_{31}NO_2$ requires: C,80.2; H,8.0; N,3.6.

EXAMPLE 3

1-Diphenylmethoxymethyl-1-(4-methoxyphenethylamino)cyclopentane

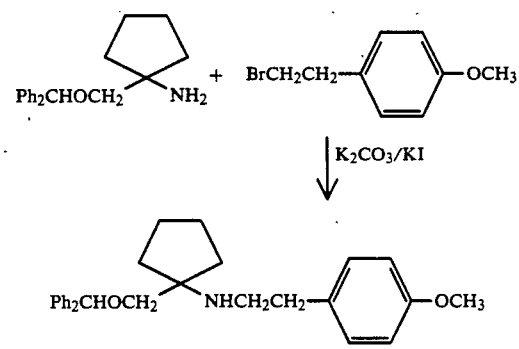

The title compound was prepared as described in Example 1 using 1-amino-1-diphenylmethoxymethylcyclopentane (see Preparation 4) and 4-methoxyphenethyl bromide. The title compound was obtained as a pale brown oil which was characterised as a hydrate (0.50 g, 49%).

Analysis %: Found: C,77.5; H,7.8; N,3.5; $C_{28}H_{33}NO_2.H_2O$ requires: C,77.6; H,8.1; N,3.2.

EXAMPLE 4

1-Diphenylmethoxymethyl-1-(4-methoxyphenethylamino)cyclohexane

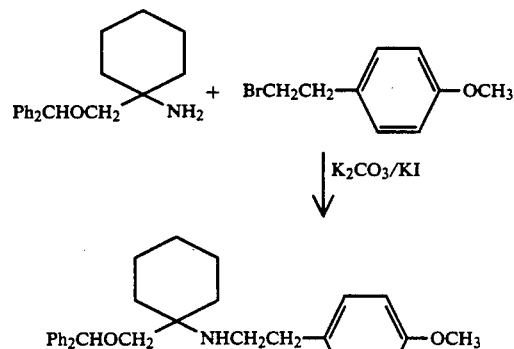

The title compound was prepared as described in Example 1 using 1-amino-1-diphenylmethoxymethylcyclohexane (see Preparation 3) and 4-methoxyphenethyl bromide. The title compound was obtained as a colourless oil (0.88 g, 68%) which was characterised from its $^1$H-n.m.r. spectrum.

$^1$H-n.m.r. (CDCl$_3$) δ=7.25-7.40 (10H, m); 7.08 (2H, d, J=8Hz); 6.87 (2H, d, J=8Hz); 5.39 (1H, s); 3.80 (3H, s); 3.60 (3H, s); 3.02-3.18 (4H, m) and 1.10-2.00 (10H, m).

EXAMPLE 5

2-{N-[2-(Benzodioxan-6-yl)ethyl]-N-methylamino}-1-(diphenylmethoxy)-2-methylpropane Method A

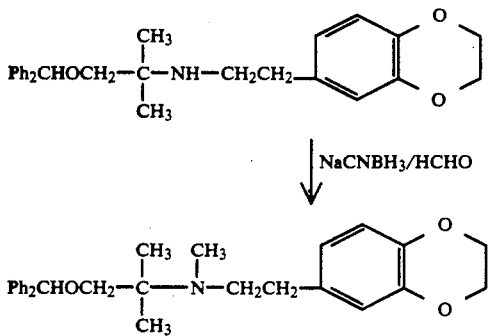

Sodium cyanoborohydride (35 mg) was added to a solution of 2-[2-(benzodioxan-6-yl)ethylamino]-1-diphenylmethoxy-2-methylpropane (209 mg — see Example 1) and 37% aqueous formaldehyde solution (50 μl) in methanol (10 ml) and the mixture was stirred at room temperature for 19 hours and evaporated. The residue was partitioned between ethyl acetate and 0.05M aqueous sodium hydroxide solution and the organic layer was washed with water, dried over sodium sulphate and evaporated. The residue was purified by chromatography on silica (8 g) using ethyl acetate plus 0-5% methanol as the eluant. Appropriate fractions were combined and evaporated to give the title compound as a colourless gum which was characterised as a hydrate (195 mg, 45%).

Analysis %: Found: C,75.4; H,7.6; N, 3.3; C$_{28}$H$_{33}$NO$_3$.H$_2$) requires: C,74.8; H,7.8; N,3.1.

Method B

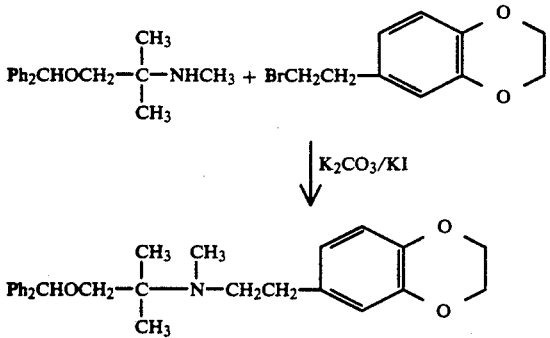

A mixture of 1-diphenylmethoxy-2-methyl-2-(methylamino)propane (2.69 g — see Preparation 5), 6-(2-bromoethyl)benzodioxan (2.43 g — see Preparation 10), potassium carbonate (2.76 g) and potassium iodide (1.66 g) in acetonitrile (80 ml) was heated under reflux for 20 hours and evaporated. The residue was partitioned between ethyl acetate and water and the organic layer was washed with water, dried over sodium sulphate and evaporated. The residue was purified by chromatography on silica (25 g) using methylene chloride plus 0-5% methanol as the eluant. Appropriate fractions were combined and evaporated to give the title compound as a colourless oil (1.00 g, 23%) which was identical to the material obtained by Method A above.

$^1$H-n.m.r. (CDCl$_3$)=7.20-7.45 (10H, m); 6.61-6.84 (3H, m); 5.32 (1H, s); 4.27 (4H, s); 3.36 (2H, s); 2.61-2.75 (4H, m); 2.40 (3H, s) and 1.18 (6H, s).

EXAMPLE 6

1-Diphenylmethoxy-1-[N-(4-methoxyphenethyl)-N-methylamino]cyclopentane

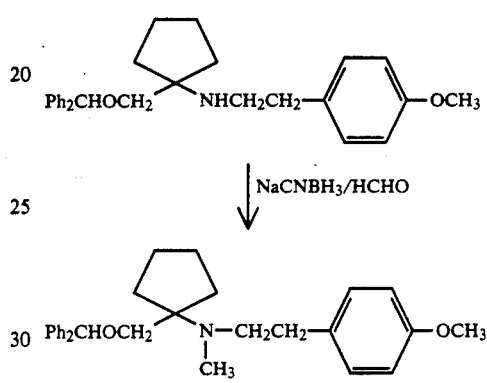

The title compound was prepared as described in Example 5, Method A, using 1-diphenylmethoxymethyl-1-(4-methoxyphenethylamino)cyclopentane (see Example 3) and sodium cyanoborohydride/formaldehyde. The title compound was obtained as a colourless oil (108 mg, 24%).

Analysis %: Found: C,80.7; H,8.1; N,3.3; C$_{29}$H$_{35}$NO$_2$ requires: C,81.1; H,8.2; N,3.3.

EXAMPLE 7

1-Diphenylmethoxymethyl-1-[N-(4-methoxyphenethyl)-N-methylamino]-cyclohexane

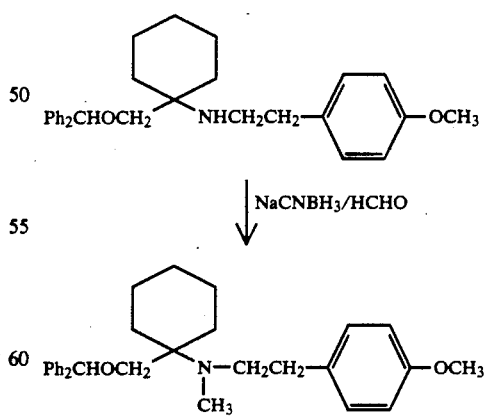

The title compound was prepared as described in Example 5, Method A, using 1-diphenylmethoxymethyl-1-(4-methoxyphenethylamino)cyclohexane (see Example 4) and sodium cyanoborohydride/formaldehyde. The title compound was obtained as a colourless oil (0.58 g, 66%), which was characterised from its $^1$H-n.m.r. spectrum.

$^1$H-n.m.r. (CDCl$_3$) δ=7.21-7.43 (10H, m); 7.12 (2H, d, J=8Hz); 6.85 (2H, d, J=8Hz); 5.23 (1H, s); 3.84 (3H, s); 3.37 (2H, s); 2.66-2.84 (4H, m); 2.41 (3H, s) and 1.20-1.85 (10H, m).

EXAMPLE 8

1-Diphenylmethoxy-2-[N-(4-methoxyphenethyl)-N-methylamino]-2-methylpropane

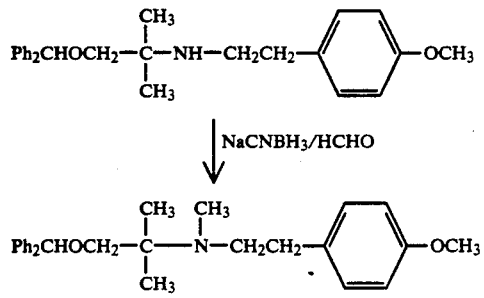

The title compound was prepared as described in Example 5, Method A, using 1-diphenylmethoxy-2-(4-methoxyphenethylamino)-2-methylpropane (see Example 2) and sodium cyanoborohydride/formaldehyde. The title compound was obtained as a colourless oil (200 mg, 69%).

Analysis %: Found: C,80.5; H,8.3; N,3.5; C$_{27}$H$_{33}$NO$_2$ requires: C,80.4; H,8.2; N,3.5.

EXAMPLES 9-35

The following compounds were prepared as described in Example 5, Method B, by reacting 1-diphenylmethoxy-2-methyl-2-(methylamino)propane (see Preparation 5) with the appropriate alkylating agent of the formula Q-(CH$_2$)$_m$-Y-R. The compounds were characterised in the forms indicated. For those products which were characterised as hydrochloride salts, the free base was dissolved in ether and the resulting solution treated with an excess of saturated ethereal hydrogen chloride. The resulting solid was collected, washed with ether and dried to give the hydrochloride salt.

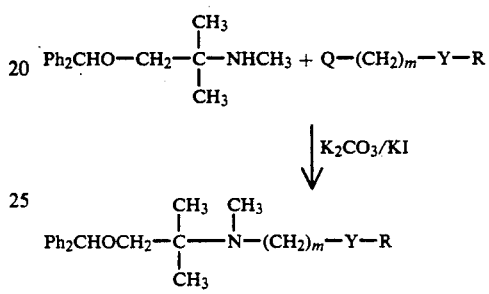

| Example No. | m | Q | —Y—R | Form Characterised | Analysis % (Theoretical in brackets) C | H | N |
|---|---|---|---|---|---|---|---|
| 9 | 2 | Br | 4-Me-C$_6$H$_4$ | Free base, oil | 83.6 (83.7 | 8.6 8.6 | 4.1 3.6) |
| 10 | 2 | Br | 4-OH-C$_6$H$_4$ | Free base, oil | 79.8 (80.2 | 8.0 8.1 | 3.5 3.6) |
| 11 | 2 | Br | 4-F-C$_6$H$_4$ | Free base, oil | 79.4 (79.8 | 7.7 7.7 | 3.5 3.6) |
| 12 | 2 | Cl | 4-SO$_2$NH$_2$-C$_6$H$_4$ | Free base, oil | 68.8 (69.0 | 7.4 7.1 | 6.3 6.2) |
| 13 | 2 | Br | 4-CO$_2$Me-C$_6$H$_4$ | Free base, oil | 77.8 (77.9 | 7.7 7.7 | 3.0 3.2) |
| 14 | 2 | MeSO$_2$O— | 4-NHSO$_2$Me-C$_6$H$_4$ | Free base, oil | 69.4 (69.5 | 7.4 7.3 | 6.1 6.0) |
| 15 | 2 | Br | 4-Br-C$_6$H$_4$ | Free base, oil | 69.0 (69.0 | 6.6 6.7 | 3.4 3.1) |

-continued

| Example No. | m | Q | —Y—R | Form Characterised | Analysis % (Theoretical in brackets) | | |
|---|---|---|---|---|---|---|---|
| | | | | | C | H | N |
| 16 | 2 | Br | 3-Me-phenyl | Free base, oil | 83.8 (83.7 | 8.9 8.6 | 3.5 3.6) |
| 17 | 2 | Br | benzo[1,3]dioxole | Free base, oil | 77.3 (77.7 | 7.7 7.5 | 3.4 3.3) |
| 18 | 2 | Br | 3-OMe-phenyl | Free base, oil | 80.1 (80.4 | 8.2 8.2 | 3.8 3.5) |
| 19 | 2 | Br | 2-thienyl | Free base, oil | 75.9 (75.9 | 7.6 7.7 | 3.8 3.7) |
| 20 | 2 | Br | 4-COCH$_3$-phenyl | Free base, oil | 80.6 (80.9 | 7.7 8.0 | 3.3 3.4) |
| 21 | 2 | Br | 3-thienyl | Free base, oil | 75.4 (75.9 | 7.5 7.7 | 3.7 3.7) |
| 22 | 1 | Cl | 3-OMe-phenyl | Hydrochloride, m.p. 169° | 73.1 (73.3 | 7.6 7.6 | 3.1 3.3) |
| 23 | 1 | Br | 4-CH$_2$Br-phenyl | Hydrochloride, m.p. 171–173° | 63.8 (63.9 | 6.4 6.4 | 2.6 2.9) |
| 24 | 1 | Br | 4-CN-phenyl | Hydrochloride, m.p. 138–140° | 74.5 (74.2 | 7.1 6.9 | 6.7 6.7) |
| 25 | 1 | Br | phenyl | Hydrochloride, m.p. 146–148° | 75.8 (75.8 | 7.7 7.6 | 3.5 3.5) |
| 26 | 1 | Cl | 4-NO$_2$-phenyl | Hydrochloride, m.p. 166–168° | 67.6 (67.4 | 6.6 6.7 | 6.1 6.3) |
| 27 | 1 | Cl | 4-OMe-phenyl | Hydrochloride, m.p. 151–153° | 73.2 (73.3 | 7.4 7.6 | 3.2 3.3) |
| 28 | 1 | Cl | 4-CO$_2$Et-phenyl | Hydrochloride, foam | 71.6 (71.8 | 7.4 7.3 | 2.9 3.0) |

-continued

| Example No. | m | Q | —Y—R | Form Characterised | C | H | N |
|---|---|---|---|---|---|---|---|
| 29 | 1 | Cl | 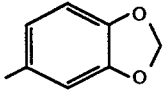 | Hydrochloride hydrate, foam | 68.4 (68.2 | 6.7 7.0 | 3.0 3.1) |
| 30 | 3 | Cl | 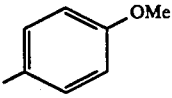 | Hydrochloride hemihydrate, foam | 72.7 (72.6 | 7.9 8.0 | 2.9 3.0) |
| 31 | 2 | Br | 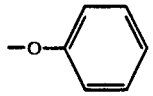 | Hydrochloride hemihydrate, foam | 71.7 (71.8 | 7.5 7.6 | 3.1 3.2) |
| 32 | 2 | Cl | 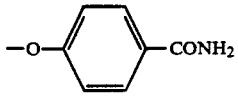 | Hydrochloride hemihydrate, foam | 68.0 (67.8 | 7.3 7.1 | 5.8 5.9) |
| 33 | 3 | Br | 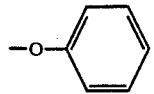 | Free base, oil | 80.1 (80.4 | 8.2 8.2 | 3.5 3.5) |
| 34 | 2 | Br | 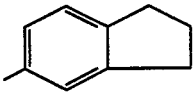 | Free base 0.25 hydrate, oil. | 83.2 (83.3 | 8.5 8.6 | 3.8 3.3) |
| 35 | 2 | Br | 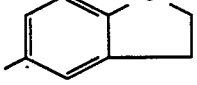 | Free base hemihydrate, oil. | 79.4 (79.2 | 7.9 8.1 | 3.2 3.3) |

EXAMPLE 36

1-[(5H)-10,11-Dihydrodibenzo[a,d]cyclohepten-5-yloxy]-2-methyl-2-[N-(3,4-methylenedioxybenzyl)-N-methylamino]propane

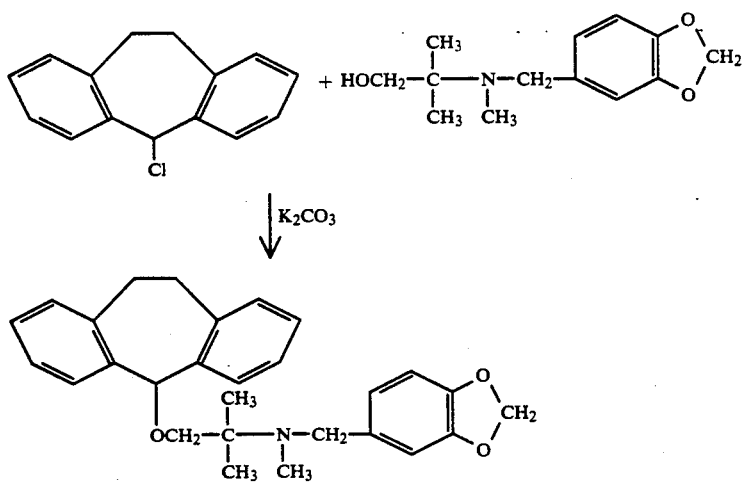

A mixture of 5chloro-(5H)-10,11-dihydrodibenzo[a,d]cycloheptane (228 mg - commercially available), 2-methyl-2-[N-(3,4-methylenedioxybenzyl)-N-methylamino]propan-1-ol (237 mg — see Preparation 8) and potassium carbonate (1.0 g) in methylene chloride was stirred at room temperature for 4 hours, filtered and evaporated. The residue was purified by chromatography on silica (5 g) using methylene chloride plus 0-2% methanol as the eluant. Appropriate fractions were combined and evaporated to give the title compound as a colourless gum which was characterised as a hemihydrate (98 mg, 22%).

Analysis %: Found: C,76.8; H,7.5; N,3.0; $C_{28}H_{31}NO_3$; 0.5 $H_2O$ requires: C,76.7; H,7.4; N,3.2.

EXAMPLES 37–39

The following compounds were prepared similarly to the procedure of Example 36 by reacting 2-[N-(4-methoxyphenethyl)-N-methylamino]-2-methylpropan-1-ol (see Preparation 7) with the appropriate alkylating agent of the formula $R^1Cl$. The alkylating agents in Examples 38 and 39 were prepared by the chlorination of the commercially available 5-hydroxy compounds with thionyl chloride.

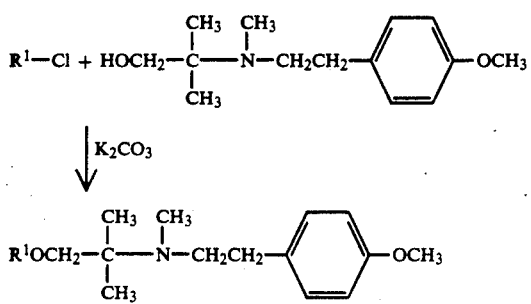

-continued

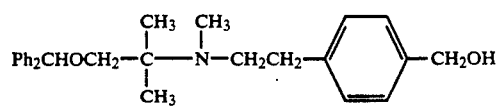

Lithium aluminium hydride (38 mg) was added to a stirred, ice-cooled solution of 1-diphenylmethoxy-2-[N-(4-methoxycarbonylphenethyl)-N-methylamino]-2-methylpropane (160 mg) (see Example 13) in ether (15 ml) and the mixture was stirred at room temperature for 17 hours, heated under reflux for 4 hours, quenched by the sequential dropwise addition with stirring of a solution of water (38 mg) in tetrahydrofuran (2 ml), 15% aqueous sodium hydroxide solution (38 mg) and water (114 mg), stirred at room temperature for 30 minutes and filtered. The filtrate was washed with 5% aqueous sodium carbonate solution and water, dried over magnesium sulphate and evaporated. The residue was purified by chromatography on silica (17 g) using hexane:n-propanol: saturated methanolic ammonia (95:5:1) as the eluant. Appropriate fractions were combined and evaporated to give the title compound as a colourless oil (130 mg, 87%).

Analysis %:
Found: C,80.5; H,8.4; N,3.6; $C_{27}H_{33}NO_2$ requires: C,80.4; H,8.2; N,3.5.

| Example No. | $R^1$ | Form characterised | Analysis % (Theoretical in brackets) | | |
|---|---|---|---|---|---|
| | | | C | H | N |
| 37 | (dibenzocycloheptane) | Free base, oil | 81.1 (81.1 | 8.6 8.2 | 3.4 3.3) |
| 38 | (dibenzocycloheptene) | Free base containing 0.33 molar equivalents of $H_2O$, oil | 80.6 (80.3 | 7.8 7.8 | 3.2 3.2) |
| 39 | (dibenzothiepine) | Free base, oil | 75.3 (75.1 | 7.3 7.4 | 3.0 3.1) |

EXAMPLE 40

1-Diphenylmethoxy-2-[N-(4-hydroxymethylphenethyl)-N-methylamino]-2-methylpropane

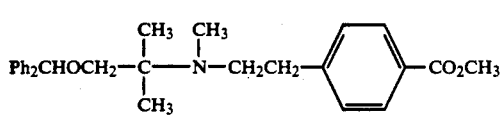

EXAMPLE 41

1-Diphenylmethoxy-2-[N-(4-hydroxymethylbenzyl)-N-methylamino]-2-methylpropane hydrochloride

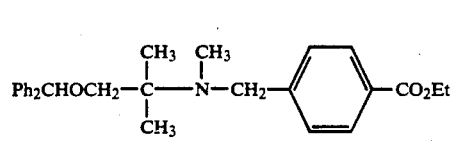

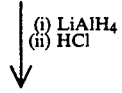

-continued

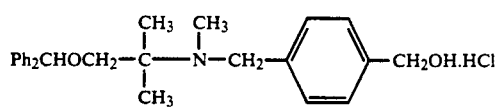

The free base of the title compound was prepared similarly to the procedure of Example 40 using 1-diphenylmethoxy-2-[N-(4-ethoxycarbonylbenzyl)-N-methylamino]-2-methylpropane (see Example 28) and lithium aluminium hydride. The resulting oil was dissolved in ether and the solution treated with an excess of saturated ethereal hydrogen chloride. The resulting precipitated oil was collected, washed with ether and dried to give the title compound as a colourless foam which was characterised as a hydrochloride containing 0.25 molar equivalents of water (377 mg, 38%).

Analysis %: Found: C,72.6; H,7.6; N,3.1; $C_{26}H_{31}NO_2;HCl;0.25\ H_2O$ requires: C,72.5; H,7.6; N,3.2.

EXAMPLE 42

2-[N-(4-Carbamoylphenethyl)-N-methylamino]-1-diphenylmethoxy-2-methylpropane

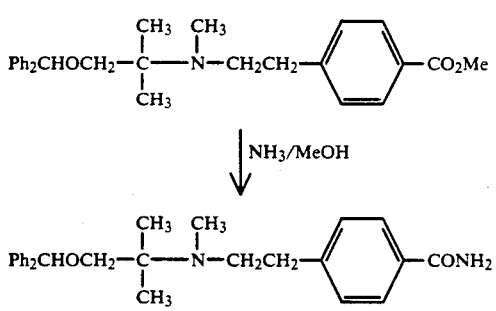

A solution of 1-diphenylmethoxy-2-[N-(4-methoxycarbonylphenethyl)-N-methylamino]-2-methylpropane (800 mg — see Example 13) in saturated methanolic ammonia (80 ml) was heated in a steel bomb at 100° for 80 hours and evaporated. The residue was purified by chromatography on silica (40 g) using methylene chloride:methanol:saturated methanolic ammonia (96:4:1) as the eluant. Appropriate fractions were combined and evaporated to give the title compound as a colourless oil (480 mg, 62%).

Analysis %: Found: C,77.5; H,7.9; N,6.7; $C_{27}H_{32}N_2O_2$ requires: C,77.8; H,7.7; N,6.7.

EXAMPLE 43

2-[N-(4-Carboxybenzyl)-N-methylamino]-1-diphenylmethoxy-2-methylpropane hydrochloride

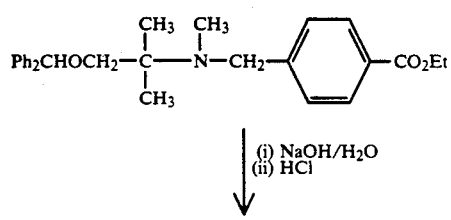

-continued

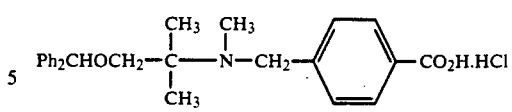

A solution of 1-diphenylmethoxy-2-[N-(4-ethoxycarbonylbenzyl)-N-methylamino]-2-methylpropane (500 mg — see Example 28) and sodium hydroxide (188 mg) in dioxan (5 ml) and water (5 ml) was heated on a steam bath for 45 minutes, acidified with glacial acetic acid and evaporated. The residue was partitioned between ether and water and the organic layer was dried over magnesium sulphate and evaporated. The residue was dissolved in ether and the solution was treated with excess saturated ethereal hydrogen chloride. The resulting precipitated oil was collected and triturated with ethyl acetate/methanol/methylene chloride to give the title compound as a colourless solid (285 mg, 61%), m.p. 238°–240°.

Analysis %: Found: C,70.5; H,6.9; N,3.0; $C_{26}H_{29}NO_3.HCl$ requires: C,71.0; H,6.9; N,3.2.

EXAMPLE 44

2-[N-(4-Carbamoylbenzyl)-N-methylamino]-1-diphenylmethoxy-2-methylpropane hydrochloride

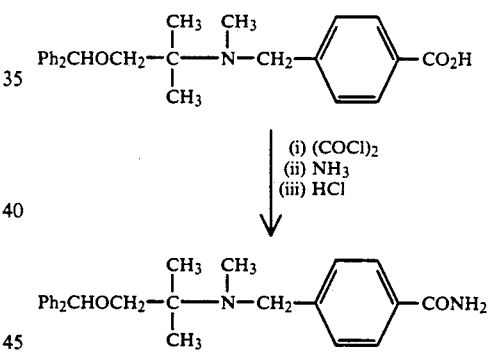

Oxalyl chloride (200 μl) was added to a solution of 2-[N-(4-carboxybenzyl)-N-methylamino]-1-diphenylmethoxy-2-methylpropane hydrochloride (300 mg — see Example 43) in methylene chloride containing two drops of dimethylformamide and the mixture was stirred at room temperature for 30 minutes. Ammonia was then bubbled through the stirred solution for 30 minutes which was then diluted with methylene chloride, washed with 10% aqueous sodium hydroxide solution, dried over magnesium sulphate and evaporated. The residue was dissolved in ether and the solution was treated with excess saturated ethereal hydrogen chloride. The resulting precipitated oil was collected, washed with ether and dried to give the title compound as a colourless foam which was characterised as containing 0.75 molar equivalents of water (63 mg, 23%).

Analysis %: Found: C,69.1; H,7.2; N,6.2; $C_{26}H_{30}N_2O_2$; HCl; 0.75 $H_2O$ requires: C,69.0; H,7.2; N,6.2.

EXAMPLE 45

2-[N-(4-Aminomethylphenethyl)-N-methylamino]-1-diphenylmethoxy-2-methylpropane

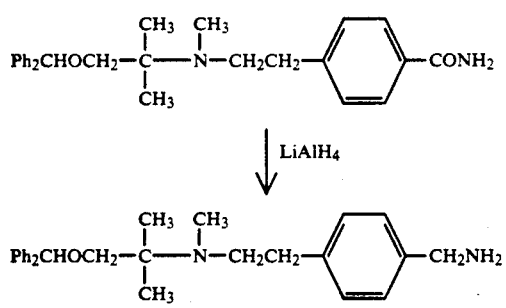

Lithium aluminium hydride (57 mg) was added to a solution of 2-[N-(4-carbamoylphenethyl)-N-methylamino]-1-diphenylmethoxy-2-methylpropane (170 mg — see Example 42) in tetrahydrofuran (12 ml) and the mixture was stirred at room temperature for 17 hours, heated under reflux for 2 hours, quenched by the sequential dropwise addition with stirring of a solution of water (57 mg) in tetrahydrofuran (1 ml), 15% aqueous sodium hydroxide solution (57 mg) and water (156 mg), stirred at room temperature for 30 minutes and filtered. The filtrate was evaporated and the residue was partitioned between methylene chloride and 5% aqueous sodium carbonate solution. The organic layer was washed with water, dried over magnesium sulphate and evaporated. The residue was purified by chromatography on silica (17 g) using hexane:ether:diethylamine (90:5:5) as the eluant. Appropriate fractions were combined and evaporated to give the title compound as a colourless oil (86 mg, 52%).

Analysis %: Found: C,80.4; H,8.5; N,6.8; $C_{27}H_{34}N_2O$ requires: C,80.6; H,8.5; N,7.0.

EXAMPLE 46

2-[N-(4-Aminomethylbenzyl)-N-methylamino]-1-diphenylmethoxy-2-methylpropane dihydrochloride

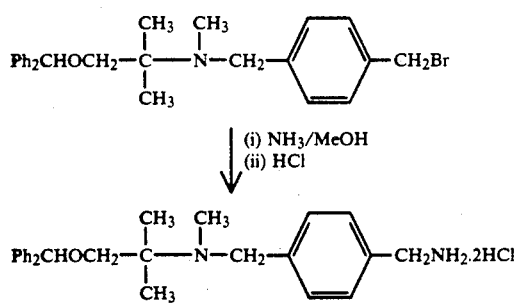

A solution of 2-[N-(4-bromomethylbenzyl)-N-methylamino]-1-diphenylmethoxy-2-methylpropane hydrochloride (800 mg — see Example 23) in saturated methanolic ammonia (40 ml) was stirred at room temperature for 18 hours and evaporated. The residue was purified by chromatography on silica (5 g) using methylene chloride plus 0-2% methanol as the eluant. Appropriate fractions were combined and evaporated to give the free base of the title compound (310 mg, 45%) as a colourless oil which was used directly in Example 47. A small portion of the residue was dissolved in ether and the solution was treated with excess saturated ethereal hydrogen chloride. The resulting precipitated oil was collected and triturated with acetone to give the title compound as a colourless foam.

Analysis %: Found: C,67.3; H,7.5; N, 6.2; $C_{26}H_{32}N_2O;2HCl$ requires: C,67.7; H,7.4; N,6.1.

EXAMPLE 47

1-Diphenylmethoxy-2-[N-(4-methanesulphonylaminobenzyl)-N-methylamino]-2-methylpropane hydrochloride

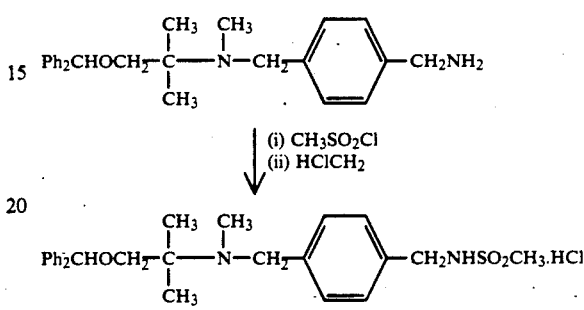

Methanesulphonyl chloride (40 μl) was added dropwise to a stirred solution of 2-[N-(4-aminomethylbenzyl)-N-methylamino]-1-diphenylmethoxy-2-methylpropane (140 mg — see Example 46) in pyridine (5 ml) and the mixture was stirred at room temperature or 16 hours and evaporated. The residue was azeotroped twice with toluene, dissolved in 2M hydrochloric acid, washed with ether, basified with saturated aqueous sodium hydrogen carbonate solution and extracted into ethyl acetate. The organic extract was dried over magnesium sulphate and evaporated. The residue was purified by chromatography on silica (3 g) using methylene chloride plus 0-5% methanol as the eluant. Appropriate fractions were combined and evaporated and the residue was dissolved in ether and treated with excess saturated ethereal hydrogen chloride. The resulting precipitated gum was collected and triturated with ether to give the title compound as a colourless solid which was characterised as a hemihydrate (31 mg, 17%), m.p. 150°-155°.

Analysis %: Found: C,63.6; H,6.9; N,5.3; $C_{27}H_{34}N_2O_3S;HCl;0.5 H_2O$ requires: C,63.3; H,7.1; N,5.5.

The following Preparations, in which all temperatures are in °C., illustrate the preparation of the novel starting materials used in the preceding Examples.

PREPARATION 1

2-Amino-1-diphenylmethoxy-2-methylpropane

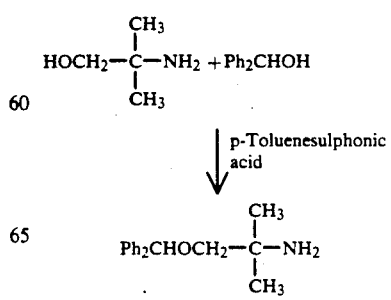

A mixture of 2-amino-2-methylpropanol (89.1 g), benzhydrol (190 g) and para-toluenesulphonic acid monohydrate (200 g) in toluene (1200 ml) was heated under reflux in a Dean-Stark apparatus for four hours and evaporated. The residue was partitioned between ether and water and the organic layer was washed with water and extracted into 10% aqueous citric acid. The acidic extract was washed with ether, basified with solid sodium carbonate and extracted into ether. The organic extract was washed with water, dried over sodium sulphate and evaporated to give the title compound as a pale yellow oil (177 g, 69%) which was characterised by its $^1$H-n.m.r. spectrum.

$^1$H-n.m.r. (CDCl$_3$) $\delta$=7.20–7.45 (10H, m); 5.39 (1H, s); 3.24 (2H, s); 1.50 (1H, broad s, exchangeable with D$_2$O) and 1.18 (6H, s).

Preparation 2

2-Amino-1-diphenylmethoxy-2-methylpropane trifluoroacetate

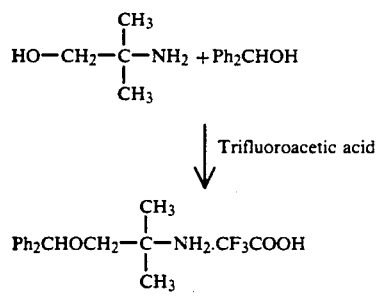

Trifluoroacetic acid (25 ml) was added to a solution of benzhydrol (9.2 g) and 2-amino-2-methylpropanol (4.5 g) in methylene chloride (5 ml) and the mixture was stirred at room temperature for 3 hours and evaporated. The residue was partitioned between water and ethyl acetate and the organic layer was washed with water, dried over magnesium sulphate and evaporated. The residue was triturated with hexane and recrystallised from ethyl acetate to give the title compound as a colourless solid (2.98 g, 16%), m.p. 160°–161°.

Analysis %: Found: C,61.7; H,6.0; N,3.6; C$_{17}$H$_{21}$NO;CF$_3$CO$_2$H requires: C,61.8; H,6.0; N,3.8.

The trifluoroacetate salt can then be converted to the free base form (see also Preparation 1) by stirring it in a suitable organic solvent, e.g. ethyl acetate or methylene chloride, with excess aqueous sodium or potassium hydroxide.

PREPARATION 3

1-Amino-1-diphenylmethoxymethylcyclohexane

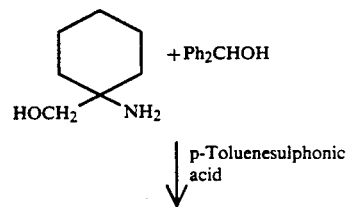

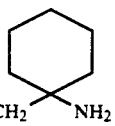

This was prepared as described in Preparation 1 using 1-aminocyclohexane-1-methanol and benzhydrol. The title compound was obtained as a pale yellow oil (2.02 g, 68%), which was characterised by its $^1$H-n.m.r. spectrum.

$^1$H-n.m.r. (CDCl$_3$) $\delta$=7.20–7.45 (10H, m); 5.38 (1H, s); 3.26 (2H, s) and 1.20–1.70 (10H, m).

PREPARATION 4

1-Amino-1-diphenylmethoxymethylcyclopentane

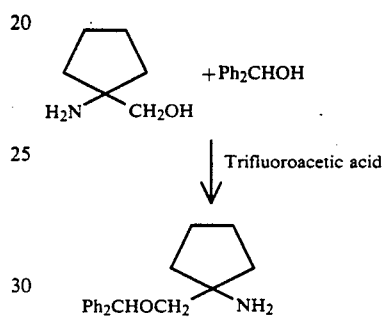

Benzhydrol (1.6 g) was added in one portion to a solution of 1-aminocyclopentane-1-methanol (1.0 g) and trifluoroacetic acid (3.5 ml) in methylene chloride (10 ml) and the mixture was stirred at room temperature for 3 hours and then treated with dioxane (10 ml) and 4M aqueous sodium hydroxide solution. The mixture was stirred at room temperature for 30 minutes and evaporated. The residue was partitioned between water and ether and the organic layer was extracted into 2M hydrochloric acid. The acidic extract was washed with ether/hexane (1:1), basified with solid sodium carbonate and extracted into ether. The organic extracts were dried over magnesium sulphate and evaporated to give the title compound as a pale yellow oil which was characterised as containing 0.25 molar equivalents of water (710 mg, 30%).

Analysis %: Found: C,79.8; H,7.9; N,4.9; C$_{19}$H$_{23}$NO;0.25 H$_2$O requires: C,79.8; H,8.3; N,4.9.

PREPARATION 5

(a)

1-Diphenylmethoxy-2-formylamino-2-methylpropane

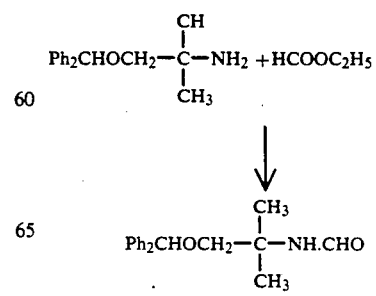

A mixture of 2-amino-1-diphenylmethoxy-2-methylpropane (7.6 g — see Preparation 1) and ethyl formate (6.7 g) was heated at 100° in a steel bomb for 18 hours and evaporated. The residue was purified by chromatography on silica (18 g) using hexane plus 0–100% methylene chloride as the eluant. Appropriate fractions were combined and evaporated to give the title compound as a colourless gum (8.4 g, 99%).

Analysis %: Found: C,76.5; H,7.8; N,4.6; $C_{18}H_{21}NO_2$ requires: C,76.3; H,7.5; N,4.9.

(b)
1-Diphenylmethoxy-2-methyl-2-(methylamino)propane

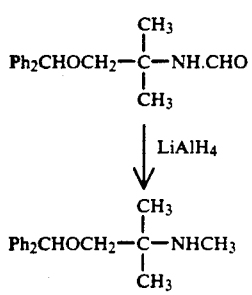

A solution of 1-diphenylmethoxy-2-formylamino-2-methylpropane (8.2 g) in ether (50 ml) was added to a suspension of lithium aluminium hydride (2.2 g) in ether (100 ml) at a rate which maintained a gentle reflux. The mixture was stirred at room temperature for 18 hours, quenched by the sequential dropwise addition of water (2.2 ml), 5M aqueous sodium hydroxide solution (2.2 ml) and water (6.6 ml) and filtered. The filtrate was dried over sodium sulphate and evaporated to give the title compound as a colourless gum (7.5 g, 96%).

Analysis %: Found: C,80.3; H,8.8; N,4.9; $C_{18}H_{23}NO$ requires: C,80.2; H,8.6; N,5.2.

PREPARATION 6

2-(4-Methoxyphenethylamino)-2-methylpropanol

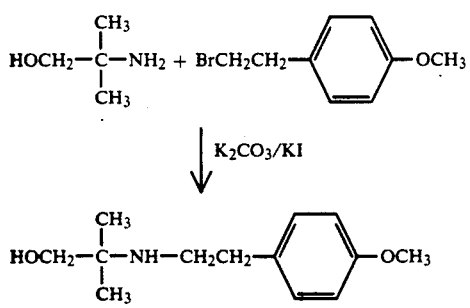

A mixture of 2-amino-2-methylpropanol (4.46 g), 4-methoxyphenethyl bromide (10.76 g), potassium carbonate (13.8 g) and potassium iodide (8.3 g) in acetonitrile (100 ml) was heated under reflux for 20 hours and evaporated. The residue was partitioned between ethyl acetate and water and the organic layer was dried over sodium sulphate and evaporated. The residual solid was recrystallised from ethyl acetate/hexane to give the title compound (6.6 g, 60%), m.p. 114°–115°.

Analysis %: Found: C,70.1; H,9.8; N,6.2; $C_{13}H_{21}NO_2$ requires: C,69.9; H,9.5; N,6.3.

PREPARATION 7

2-[N-(4-Methoxyphenethyl)-N-methylamino]-2-methylpropanol

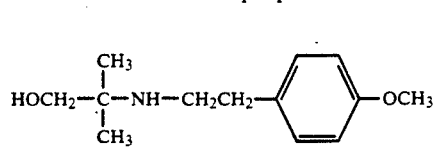

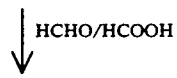

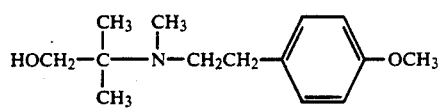

37% Aqueous formaldehyde solution (2.68 g) was added to a stirred solution of 2-(4-methoxyphenethylamino)-2-methylpropanol (3.35 g — see Preparation 6) in formic acid (3.45 g) and the mixture was heated under reflux for 2.5 hours, acidified with 2M hydrochloric acid, washed with ether, basified with solid sodium hydroxide and extracted into ethyl acetate. The organic extract was dried over sodium sulphate and evaporated. The residue was triturated with hexane to give the title compound as a colourless solid (3.20 g, 90%), m.p. 40°.

Analysis %: Found: C,71.1; H,10.0; N,6.0: $C_{14}H_{23}NO_2$ requires: C,70.8; H,9.8; N,5.9.

PREPARATION 8

2-Methyl-2-[N-(3,4-methylenedioxybenzyl)-N-methylamino]propanol hydrochloride

A mixture of 2-methyl-2-methylaminopropanol (1.5 g), 3,4-methylenedioxybenzyl chloride (2.5 g) and potassium carbonate (2 g) in acetonitrile (50 ml) was heated under reflux for 4 hours and evaporated. The residue was partitioned between ether and 2M hydrochloric acid and the acidic layer was washed with methylene chloride, basified with 10% aqueous sodium carbonate solution and extracted into methylene chloride. The organic extract was dried over magnesium sulphate and evaporated to give essentially pure 2-methyl-2-[N-(3,4-methylenedioxybenzyl)-N-methylamino]propanol as a yellow oil (2.0 g, 58%) which was used directly in Example 34. A small portion of this product was dissolved in ether and the solution was treated with excess saturated ethereal hydrogen chloride and evaporated. The residue was triturated with acetone/ethyl acetate to give the title compound as a colourless solid, m.p. 157°-159°.

Analysis %: Found: C,56.9; H,7.4; N,5.1; C₁₃H₁₉NO₃;HCl requires: C,57.0; H,7.4; N,5.1.

PREPARATION 9

(a) 3,4-Methylenedioxyphenethyl alcohol

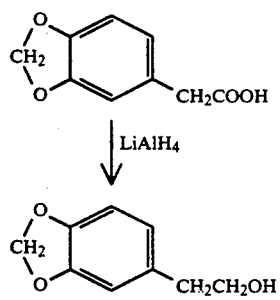

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%) which was characterised by its ¹H-n.m.r. spectrum.

¹H-n.m.r. (CDCl₃) δ=6.69–6.83 (3H, m); 5.98 (2H, s); 3.82 (2H, dt, J=7 and 6Hz); 2.81 (2H, t, J=7Hz) and 1.44 (1H, t, J=6Hz, exchangeable with D₂O).

(b) 3,4-Methylenedioxyphenethyl bromide

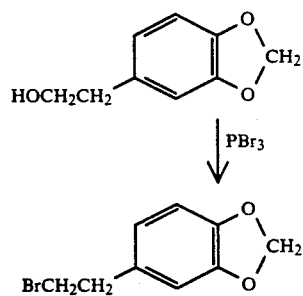

A solution of phosphorus tribromide (8.1 g) in carbon tetrachloride (50 ml) was added dropwise over 30 minutes to a stirred solution of 3,4-methylenedioxyphenethyl alcohol (15.0 g) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g, 40%), which was characterised by its ¹H-n.m.r. spectrum.

¹H-n.m.r. (CDCl₃) δ=6.80 (1H, d, J=8Hz), 6.75 (1H, s); 6.71 (1H, d, J=8Hz); 6.00 (2H, s); 3.56 (2H, t, J=7Hz) and 3.13 (2H, t, J=7Hz).

PREPARATION 10

(a) 6-(2-Hydroxyethyl)benzodioxan

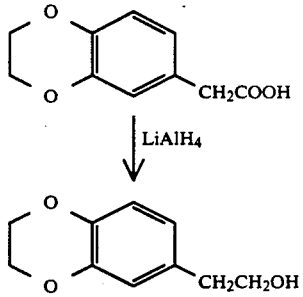

This was prepared as described in Preparation 9(a) using (benzodioxan-6-yl)acetic acid instead of 3,4-methylenedioxyphenylacetic acid. The title compound was obtained as a colourless oil (19.8 g, 92%), which was characterised by its ¹H-n.m.r. spectrum.

¹H-n.m.r. (CDCl₃) δ=6.84 (1H, d, J=8Hz); 6.77 (1H, d, J=2Hz); 6.73 (1H, dd, J=8 and 2Hz); 4.28 (4H, s); 3.59 (2H, t, J=7Hz) and 3.08 (2H, t, J=7Hz).

(b) 6-(2-Bromoethyl)benzodioxan

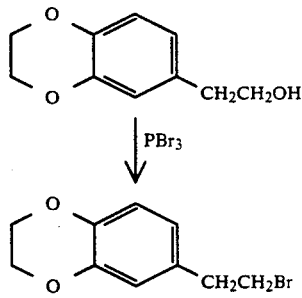

This was prepared as described in Preparation 9(b) using 6-(2-hydroxyethyl)benzodioxan instead of 3,4-methylenedioxyphenethyl alcohol. The title compound was obtained as a pale yellow oil (21.4 g, 80%), which was characterised by its ¹H-n.m.r. spectrum.

¹H-n.m.r. (CDCl₃) δ=6.83 (1H, d, J=8Hz); 6.77 (1H, d, J=2Hz); 6.72 (1H, dd, J=8 and 2Hz); 4.28 (4H, s); 3.59 (2H, t, J=7Hz) and 3.10 (2H, t, J=7Hz).

PREPARATION 11

N-[4-(2-Methanesulphonyloxyethyl)phenyl]methanesulphonamide

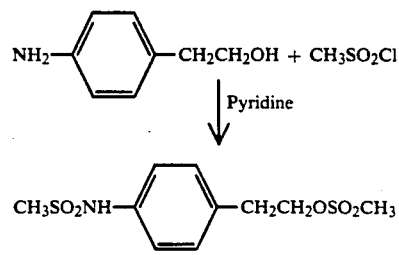

Methanesulphony chloride (50.4 g) was added dropwise to a stirred solution of 4-aminophenethyl alcohol (27.44 g) in dry pyridine (300 ml) at 0° and the solution was stirred at 0° for 30 minutes and then at room temperature for 2.5 hours. It was then poured into water and the solid was filtered off, washed with water, dried and crystallised from ethyl acetate to give the title compound (39.0 g, 66%), m.p. 136°-137°.

Analysis %: Found: C,40.6; H,5.2; N,4.9; $C_{10}H_{15}NO_5S_2$ requires: C,40.9; H,5.1; N,4.8.

PREPARATION 12

Preparation of 5-(2-bromoethyl)indane

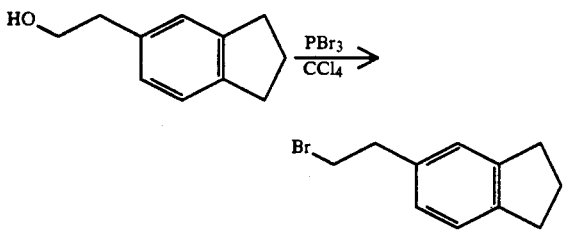

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted with dichloromethane (2×100 ml). The combined dichloromethane extracts were dried (MgSO4) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H N.M.R. (CDCl$_3$) δ=7.30–7.00 (m, 3H); 3.60 (m, 2H); 3.20 (m, 2H); 3.00–2.85 (m, 4H); 2.20–2.05 (m, 2H) ppm.

PREPARATION 13

(A) Preparation of 5-(2-hydroxyethyl)-2,3-dihydrobenzofuran

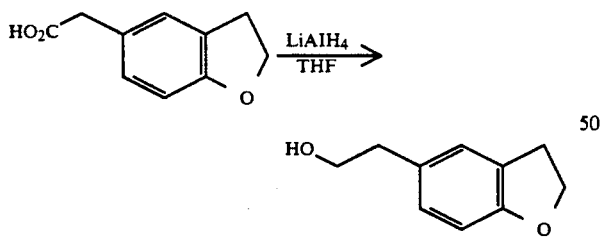

A solution of (2,3-dihydrobenzofuran-5-yl)acetic acid (4.9 g — see EP-A-132130) in anhydrous tetrahydrofuran (50 ml) was added over 10 minutes, dropwise, to a stirred suspension of lithium aluminium hydride (1.57 g) in anhydrous tetrahydrofuran (50 ml) at 0°. The mixture was allowed to warm to room temperature and stirred for 1 hour. Water (1.5 ml) was then added dropwise with caution followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H N.M.R. (CDCl$_3$) δ=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

(B) Preparation of 5-(2-bromoethyl)-2,3-dihydrobenzofuran

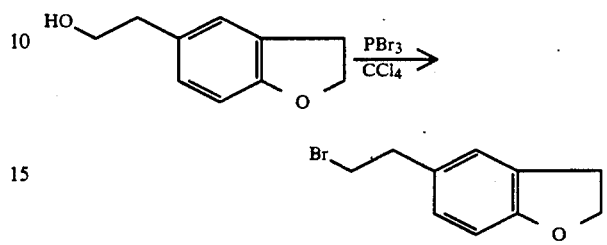

Phosphorus tribromide (0.37 g) was added to a solution of 5-(2-hydroxyethyl)-2,3-dihydrobenzofuran (0.612 g — see Part A) in carbon tetrachloride (3 ml) and the mixture heated under reflux for 3 hours. On cooling to room temperature, the mixture was partitioned between 10% aqueous sodium carbonate (20 ml) and dichloromethane (20 ml). The layers were separated and the aqueous layer extracted with dichloromethane (2×10 ml). The combined dichloromethane extracts were dried (MgSO4) and concentrated in vacuo to give the title compound as an oil which crystallised on standing, yield 0.584 g, m.p. 60°-62°.

$^1$H N.M.R. (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

We claim:
1. A compound of the formula:

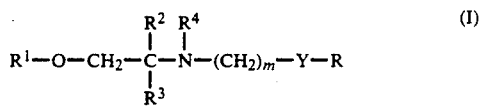

or a pharmaceutically acceptable salt thereof, wherein $R^1$ is a group of the formula:

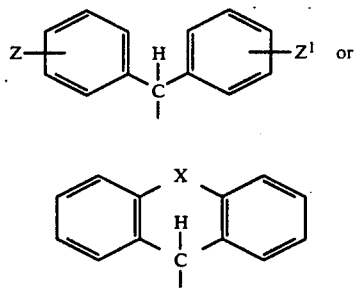

where
Z and $Z^1$ are each independently hydrogen, halo or $C_1$-$C_4$ alkyl;
X is —(CH$_2$)$_2$—, —CH=CH—, —CH$_2$—S—, —CH$_2$—O—, —S— or —O—;
Y is a direct link, O or S;
$R^2$ and $R^3$ are each independently $C_1$-$C_4$ alkyl or together represent —(CH$_2$)$_p$— where p is 2, 3, 4 or 5;
$R^4$ is H or $C_1$-$C_4$ alkyl;

m is 1, 2, or 3, with the proviso that when m is 1, Y is a direct link; and

R is a group of the formula:

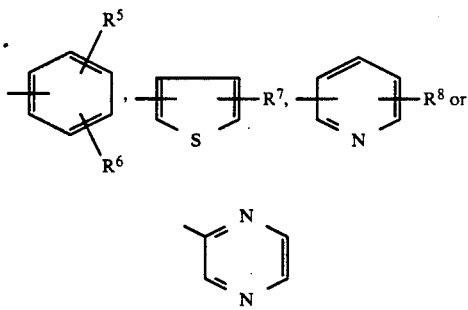

where either $R^5$ and $R^6$ are each independently hydrogen, $C_1$-$C_4$ alkyl, hydroxy—($C_1$-$C_4$ alkyl), hydroxy, $C_1$-$C_4$ alkoxy, halo, halomethyl, nitro, cyano, sulphamoyl, —CO($C_1$-$C_4$ alkyl), —OCO($C_1$-$C_4$ alkyl), —$CO_2$($C_1$-$C_4$ alkyl), carboxy, —$(CH_2)_q$CONR$^9$R$^{10}$, —$(CH_2)_q$OCONR$^9$R$^{10}$, —$(CH_2)_q$NR$^{11}$R$^{12}$ or —NHSO$_2$NH$_2$ in which R$^9$ and R$^{10}$ are each independently H or $C_1$-$C_4$ alkyl, q is 0, 1 or 2, and either R$^{11}$ and R$^{12}$ are each independently H or $C_1$-$C_4$ alkyl or R$^{11}$ is hydrogen and R$^{12}$ is —SO$_2$($C_1$-$C_4$ alkyl), —CO($C_1$-$C_4$ alkyl) or —CONH($C_1$-$C_4$ alkyl; or $R^5$ and $R^6$, when attached to adjacent carbon atoms, together represent a group of the formula —O($CH_2$)$_r$O— where r is 1, 2 or 3, —O($CH_2$)$_2$— or —($CH_2$)$_3$—; $R^7$ is H, $C_1$-$C_4$ alkyl or —CONH$_2$; and $R^8$ is H, $C_1$-$C_4$ alkyl or $C_1$-$C_4$ alkoxy.

2. A compound as claimed in claim 1 wherein $R^1$ is selected from:

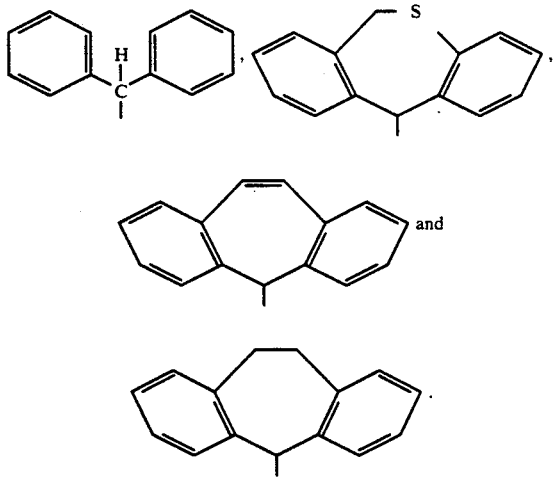

3. A compound as claimed in claim 1 wherein Y is a direct link or O.

4. A compound as claimed in claim 1 wherein m is 2.

5. A compound as claimed in claim 1 wherein $R^2$ and $R^3$ are each methyl or are taken together and represent —($CH_2$)$_4$— or —($CH_2$)$_5$—.

6. A compound as claimed in claim 1 wherein $R^4$ is H or $CH_3$.

7. A compound as claimed in claim 1 wherein R is selected from:

(a) a group of the formula:

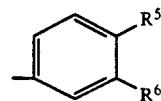

where $R^5$ and $R^6$ are as defined in claim 1, (b) unsubstituted 2- or 3-thienyl, and (c) unsubstituted pyridyl.

8. A compound as claimed in claim 7 wherein R is a group of the formula:

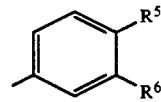

where either one of $R^5$ and $R^6$ is hydrogen and the other is hydrogen, $C_1$-$C_4$ alkoxy, $C_1$-$C_4$ alkyl, hydroxy, hydroxymethyl, halo, sulphamoyl, —CO($C_1$-$C_4$ alkoxy), carboxy, carbamoyl, —NHSO$_2$($C_1$-$C_4$ alkyl), —CH$_2$NHSO$_2$($C_1$-$C_4$ alkyl), —CO($C_1$-$C_4$ alkyl), halomethyl, cyano, nitro, or aminomethyl; or $R^5$ and $R^6$ together represent —OCH$_2$O—, —O($CH_2$)$_2$O—, —O($CH_2$)$_2$— or —($CH_2$)$_3$—.

9. A compound as claimed in claim 8 wherein R is

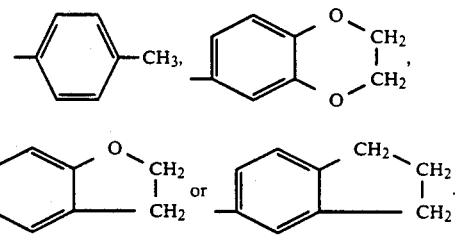

10. A compound of the formula:

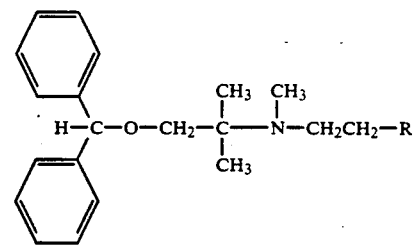

where R is 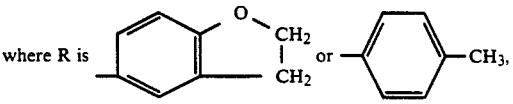

or a pharmaceutically acceptable salt thereof.

11. A pharmaceutical composition comprising a compound of the formula (I) as claimed in any one of the preceding claims, or a pharmaceutically acceptable salt thereof, and a pharmaceutically acceptable diluent or carrier.

12. A method of treating a human being to cure or prevent a disease associated with the altered motility and/or tone of smooth muscle which comprises treating said animal with an effective amount of a compound of the formula (I) or a pharmaceutically acceptable salt thereof as claimed in claim 1.

13. A method according to claim 12 of treating a human being to cure or prevent a disease selected from the group consisting of irritable bowel syndrome, diverticular disease, urinary incontinence, oesophageal achalasia, or chronic obstructive airways disease.

* * * * *